US010155991B2

(12) United States Patent
Xia

(10) Patent No.: US 10,155,991 B2
(45) Date of Patent: Dec. 18, 2018

(54) BIOMARKERS FOR USE IN COLORECTAL CANCER

(71) Applicant: Xueliang James Xia, Tempe, AZ (US)

(72) Inventor: Xueliang James Xia, Tempe, AZ (US)

( * ) Notice: Subject to any disclaimer, the term of this patent is extended or adjusted under 35 U.S.C. 154(b) by 24 days.

(21) Appl. No.: 14/912,018

(22) PCT Filed: Aug. 15, 2013

(86) PCT No.: PCT/US2013/055207
§ 371 (c)(1),
(2) Date: Feb. 12, 2016

(87) PCT Pub. No.: WO2015/023285
PCT Pub. Date: Feb. 19, 2015

(65) Prior Publication Data

US 2016/0201136 A1 Jul. 14, 2016

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

2007/0054295 A1* 3/2007 Spivack ................. C12Q 1/686
435/6.12

OTHER PUBLICATIONS

Yi et al. Cancer Res. 2008. 68(19):8094-8103.*
Suzuki et al. Nature Genetics. 2004. 36(4):417-422.*
Warren et al. BMC Medicine. 2011. 9:133.*
Feng et al. PNAS. 2010. 107(19):8689-8694.*
Tan et al. Carcinogenesis. 2002. 23(2):231-236.*

* cited by examiner

*Primary Examiner* — Joseph G. Dauner

(57) ABSTRACT

The present invention provides assays, methods and kits that may be used to assess colorectal cancer (CRC) in a subject in relation to diagnosis, prognosis and treatment evaluation, using blood samples.

2 Claims, No Drawings

Specification includes a Sequence Listing.

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 1

ttttgatttt tagtgttgcg                                          20


<210> SEQ ID NO 2
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 2

tttttgattt ttagtgttgt g                                        21


<210> SEQ ID NO 3
<211> LENGTH: 18
<212> TYPE: DNA
<213> ORGANISM: Artificial Sequence
<220> FEATURE:
<223> OTHER INFORMATION: Synthetic primer for modified gene sequence
```

<400> SEQUENCE: 3
aatttaatct atccctac 18

<210> SEQ ID NO 4
<211> LENGTH: 18
<212> TYPE: DNA
<213> ORGANISM: Artificial Sequence
<220> FEATURE:
<223> OTHER INFORMATION: Synthetic primer for modified gene sequence

<400> SEQUENCE: 4
aatttaatct atccctac 18

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer for modified gene sequence

<400> SEQUENCE: 5
agttttttag ttagatttcg 20

<210> SEQ ID NO 6
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 6
gagtttttta gttagatttt g 21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 7
aacaaaataa actcacaaaa 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 8
aacaaaataa actcacaaaa 20

<210> SEQ ID NO 9
<211> LENGTH: 18
<212> TYPE: DNA
<213> ORGANISM: Artificial Sequence
<220> FEATURE:
<223> OTHER INFORMATION: Synthetic primer for modified gene sequence

<400> SEQUENCE: 9
ggtatattag ttagttcg 18

<210> SEQ ID NO 10
<211> LENGTH: 19

<212> TYPE: DNA
<213> ORGANISM: Artificial Sequence
<220> FEATURE:
<223> OTHER INFORMATION: Synthetic primer for modified gene sequence

<400> SEQUENCE: 10
gggtatatta gttagtttg 19

<210> SEQ ID NO 11
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 11
aaaacaaaaa atatccccga 20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 12
aaaacaaaaa atatccccaa 20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 13
cggagttttt cggagttgcg 20

<210> SEQ ID NO 14
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 14
ttggagtttt ttggagttgt g 21

<210> SEQ ID NO 15
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 15
actaaaacgc gaaaaaacga 20

<210> SEQ ID NO 16
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 16
gactaaaaca caaaaaaaca a 21

<210> SEQ ID NO 17
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 17
cggtttattt tgtttttttcg 20

<210> SEQ ID NO 18
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 18
atggtttatt ttgttttttt g 21

<210> SEQ ID NO 19
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 19
cgaaaaaaca acgcgaacga 20

<210> SEQ ID NO 20
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 20
ccaaaaaaac aacacaaaca a 21

<210> SEQ ID NO 21
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 21
tttttcgggg tttcgagtcg 20

<210> SEQ ID NO 22
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 22
gttttttggg gttttgagtt g 21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 23
tcgtaaacgc gcgaccccga 20

<210> SEQ ID NO 24
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 24
catcataaac acacaacccc aa 22

<210> SEQ ID NO 25
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 25
gcgggttcgg gataagttcg 20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 26
gtgggtttgg gataagtttg 20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 27
caaacaacaa tacgaaacga 20

<210> SEQ ID NO 28
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 28
cccaaacaac aatacaaaac aa 22

<210> SEQ ID NO 29
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 29 ggagggggc gtttcggtcg 20

<210> SEQ ID NO 30
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 30 aggaggggg tgttttggtt g 21

<210> SEQ ID NO 31
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 31
aactaaaacc cgaataaccg 20

<210> SEQ ID NO 32
<211> LENGTH: 21
<212> TYPE: DNA
<213> ORGANISM: Artificial Sequence
<220> FEATURE:
<223> OTHER INFORMATION: Synthetic primer for modified gene sequence

<400> SEQUENCE: 32
aaactaaaac ccaaataacc a 21

<210> SEQ ID NO 33
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 33
ttttgggcgc gggttaggcg 20

<210> SEQ ID NO 34
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 34
ttttttgggt gtgggttagg tg 22

<210> SEQ ID NO 35
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 35
ctaaacacac gaccgaaacg 20

<210> SEQ ID NO 36
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 36
cctaaacaca caaccaaaac ac 22

<210> SEQ ID NO 37
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 37
tgaggtcgcg tttttcgtcg 20

<210> SEQ ID NO 38
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 38
gttgaggttg tgtttttgt tg 22

<210> SEQ ID NO 39
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 39
aatcctaaac acacgaccga 20

<210> SEQ ID NO 40
<211> LENGTH: 22
<212> TYPE: DNA
<213> ORGANISM: Artificial Sequence
<220> FEATURE:
<223> OTHER INFORMATION: Synthetic primer for modified gene sequence

<400> SEQUENCE: 40
acaatcctaa acacacaacc aa 22

<210> SEQ ID NO 41
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 41
tggtcgtagc ggggcgttcg 20

<210> SEQ ID NO 42
<211> LENGTH: 23
<212> TYPE: DNA
<213> ORGANISM: Artificial Sequence
<220> FEATURE:
<223> OTHER INFORMATION: Synthetic primer for modified gene sequence

<400> SEQUENCE: 42
atttggttgt agtggggtgt ttg 23

<210> SEQ ID NO 43

<211> LENGTH: 16
<212> TYPE: DNA
<213> ORGANISM: Artificial Sequence
<220> FEATURE:
<223> OTHER INFORMATION: Synthetic primer for modified gene sequence

<400> SEQUENCE: 43
cccgcctaac ccgcgc 16

<210> SEQ ID NO 44
<211> LENGTH: 18
<212> TYPE: DNA
<213> ORGANISM: Artificial Sequence
<220> FEATURE:
<223> OTHER INFORMATION: Synthetic primer for modified gene sequence

<400> SEQUENCE: 44
tccccaccta acccacac 18

<210> SEQ ID NO 45
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 45
atttttgtag gcgtagagcg 20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer for modified gene sequence

<400> SEQUENCE: 46
atttttgtag gtgtagagtg 20

<210> SEQ ID NO 47
<211> LENGTH: 17
<212> TYPE: DNA
<213> ORGANISM: Artificial Sequence
<220> FEATURE:
<223> OTHER INFORMATION: Synthetic primer for modified gene sequence

<400> SEQUENCE: 47 tcccttccc cgaacgc 17

<210> SEQ ID NO 48
<211> LENGTH: 18
<212> TYPE: DNA
<213> ORGANISM: Artificial Sequence
<220> FEATURE:
<223> OTHER INFORMATION: Synthetic primer for modified gene sequence

<400> SEQUENCE: 48
ctccccttcc ccaaacac 18

BIOMARKERS FOR USE IN COLORECTAL CANCER

FIELD OF THE INVENTION

The present invention generally provides compositions and methods useful for diagnostic, prognostic and therapeutic evaluation of colorectal cancers, particularly for the early diagnosis, prognosis and therapy evaluation by detecting altered methylation level of genes in a specific biomarker profile.

BACKGROUND OF THE INVENTION

Colorectal cancer (CRC) can be roughly divided into hereditary (or familial) and sporadic forms. Hereditary non-polyposis colorectal cancer (HNPCC), or Lynch syndrome, accounts for only 2 to 3 percent of colon cancer cases in the United States. Familial adenomatous polyposis (FAP) occurs in 1 in 20,000 live births and accounts for fewer than 1 percent of colon cancer cases. In contrast, the sporadic form of colon cancer, which does not have a strong genetic or hereditary component, accounts for more than eighty percent of all cases. Industrialized nations appear to have the greatest risk of CRC among their populations, and the cancer rate is still increasing. CRC is now one of the leading causes of cancer mortality worldwide. It is the third most common cancer and second most common cause of cancer deaths in all cancer patients in the United States. One of the reasons is the lack of efficient testing methods for detecting tumors and determining tumor response to therapies.

Moreover, once colon cancer has been diagnosed, it is also important to determine its stage of the cancer in order to plan treatment accordingly. The stages of colon cancer include stages 0, I, II, III and IV. Tests and procedures often used for staging include CT scan, MRI (magnetic resonance imaging), PET scan (positron emission tomography scan), chest x-ray, surgery, lymph node biopsy, complete blood count of red and white blood cells, platelets, hemoglobin etc., or carcinoembryonic antigen (CEA) assay.

Regardless of the efficacy of various therapies available, early stage screening for CRC or even precancerous lesions has been shown to be most effective for patient care in general, specifically for reduction of disease-related mortality and costs. However, most commonly used early stage screening methods do not have sufficient sensitivity and specificity, and they are often invasive and complex and thus less acceptable to patients. Recent advancements in research have shown that epigenetic methylation events are prevalent in a variety of cancers and the roles of methylation in cancers have been widely studied, however, many of the tests based on epigenetic methylations associated with colorectal cancer are applicable only in tumor biopsy tissues. These tests therefore have limited use because, as is widely known, traditional surgical biopsy and imaging technologies for colorectal cancers have many limitations, as they are invasive, and impose a risk of infection and persistent adverse effects to patients undergoing the procedures. Therefore, a screening test that diagnoses and evaluates CRC, and the predisposition thereof, in a sensitive, specific, and compliant way is greatly needed.

SUMMARY OF THE INVENTION

One aspect of the present invention provides a method of using a profile of biomarkers, for which the level of methylation is important and significant in assessing the CRC stages, development, and responses to treatment. More importantly, the testing method based on this marker profile allows the detection of circulating methylated biomarkers in whole blood, blood serum, or plasma, which provides a non-invasive and desirable approach for diagnosing CRC, and monitoring cancer progression and response to therapies. In the present invention, obtaining an assay operable with a blood sample is essential not only for the various advantages of such a method in a clinical setting, but for overcoming the difficulty facing the industry as well: not all biomarkers are intact in blood because of possible degradation, and not all biomarkers perform similarly satisfying with different sample types.

The present invention generally provides a method of assessing colorectal cancer (CRC) in a subject. The method comprises (1) obtaining a blood sample from the subject; (2) subjecting the blood sample to conditions that allow nucleic acid amplification to produce amplification products specific to the methylation status of at least one biomarker of a CRC biomarker profile operable in blood samples; and (3) identifying amplification products specific to a methylated CRC biomarker operable in the blood sample, wherein the existence of such amplification products indicates an occurrence of CRC in the subject, and wherein the non-existence of such amplification products indicates no occurrence of CRC in the subject. An occurrence of CRC, as defined herein, include the presence of detectable CRC at any stage as well as a predisposition or being at an elevated risk of developing CRC in comparison to an individual that does not have methylated biomarker of the CRC biomarker profile operable in blood samples. In addition, when the occurrence of CRC is assessed in a number of samples collected from a patient along a time line under a CRC treatment, a change in methylation status of one or more biomarkers in the CRC biomarker profile operable in blood samples can be used to evaluate the effectiveness of the treatment. As such, a reduction of methylation of one or more biomarker of the CRC biomarker profile operable in a blood sample at a point of time, in comparison to samples from a prior point of time, indicating that the treatment is responsive; whereas an increase of methylation of one or more biomarker of the CRC biomarker profile operable in a blood sample at a point of time, in comparison to samples from a prior point of time, indicating that the treatment is not responsive. In this method, the CRC biomarker profile operable in the blood sample comprises PROM1, SARP1, MSF1, and combinations thereof. Therefore, in one embodiment, one may produce amplification products specific to the methylation status of PROM1 in order to assess the occurrence of CRC in a patient. In another embodiment, one may produce amplification products specific to the methylation status of SARP1 in order to assess the CRC in a patient. Yet in another embodiment, one may produce amplification products specific to the methylation status of MSF1 in order to assess the CRC in a patient. In still another embodiment, one may produce amplification products specific to the methylation status of PROM1 and amplification products specific to the methylation status of SARP1 in order to assess the CRC in a patient. In yet another embodiment, one may produce amplification products specific to the methylation status of PROM1 and amplification products specific to the methylation status of MSF1 in order to assess the CRC in a patient. In a further embodiment, one may produce amplification products specific to the methylation status of MFS1 and amplification products specific to the methylation status of SARP1 in order assess the CRC in a patient. In another embodiment, one may produce amplification products specific to the methylation status of PROM1, amplification products specific to the methylation status of SARP1, and amplification products specific to the methylation status of MFS1, in order to assess the CRC in a patient.

In the method provided herein, the methylation status of PROM1 is detectable by a primer mixture comprising at least one primer pair specific to methylated PROM1, and such a primer mixture may further comprise a primer pair specific to unmethylated PROM1. As provided herein, the primer pair specific to methylated PROM1 is preferably selected from the group consisting of a primer pair having one primer comprising SEQ ID NO. 1 and the other comprising SEQ ID NO. 3; a primer pair having one primer comprising SEQ ID NO. 5 and the other comprising SEQ ID NO. 7; and a primer pair having one primer comprising SEQ ID NO. 9 and the other comprising SEQ ID NO. 11. Further, the primer pair specific to unmethylated PROM1 is selected from the group consisting of a primer pair having one primer comprising SEQ ID NO. 2 and the other comprising SEQ ID NO. 4; a primer pair having one primer comprising SEQ ID NO. 6 and the other comprising SEQ ID NO. 8; and a primer pair having one primer comprising SEQ ID NO. 10 and the other comprising SEQ ID NO. 12.

In the method provided herein, the methylation status of SARP1 is detectable by a primer mixture comprising at least one primer pair specific to methylated SARP1, and such a primer mixture may further comprise a primer pair specific to unmethylated SARP1. As provided herein, the primer pair specific to methylated SARP1 is preferably selected from the group consisting of a primer pair having one primer comprising SEQ ID NO. 13 and the other comprising SEQ ID NO. 15; a primer pair having one primer comprising SEQ ID NO. 17 and the other comprising SEQ ID NO. 19; a primer pair having one primer comprising SEQ ID NO. 21 and the other comprising SEQ ID NO. 23; and a primer pair having one primer comprising SEQ ID NO. 25 and the other comprising SEQ ID NO. 27. Further, the primer pair specific to unmethylated SARP1 is selected from the group consisting of a primer pair having one primer comprising SEQ ID NO. 14 and the other comprising SEQ ID NO. 16; a primer pair having one primer comprising SEQ ID NO. 18 and the other comprising SEQ ID NO. 20; a primer pair having one primer comprising SEQ ID NO. 22 and the other comprising SEQ ID NO. 24; and a primer pair having one primer comprising SEQ ID NO. 26 and the other comprising SEQ ID NO. 28.

In the method provided herein, the methylation status of MSF1 is detectable by a primer mixture comprising at least a primer pair specific to methylated MSF1, and such a primer mixture may further comprise a primer pair specific to unmethylated MSF1. As provided herein, the primer pair specific to methylated MSF1 is preferably selected from the group consisting of a primer pair having one primer comprising SEQ ID NO. 29 and the other comprising SEQ ID NO. 31; a primer pair having one primer comprising SEQ ID NO. 33 and the other comprising SEQ ID NO. 35; a primer pair having one primer comprising SEQ ID NO. 37 and the other comprising SEQ ID NO. 39; a primer pair having one primer comprising SEQ ID NO. 41 and the other comprising SEQ ID NO. 45; and a primer pair having one primer comprising SEQ ID NO. 41 and the other comprising SEQ ID NO. 47. Additionally, the primer pair specific to unmethylated MSF1 is selected from the group consisting of a primer pair having one primer comprising SEQ ID NO. 30 and the other comprising SEQ ID NO. 32; a primer pair having one primer comprising SEQ ID NO. 34 and the other comprising SEQ ID NO. 36; a primer pair having one primer comprising SEQ ID NO. 38 and the other comprising SEQ ID NO. 40; a primer pair having one primer comprising SEQ ID NO. 42 and the other comprising SEQ ID NO. 44; and a primer pair having one primer comprising SEQ ID NO. 46 and the other comprising SEQ ID NO. 48.

When using any of the above methods to assess a subject regarding CRC, the methylated PROM1, or SARP1, or MSF1, or any combination thereof, indicates the occurrence of CRC at a certain stage in the subject. The occurrence of CRC determined using the present method can be further verified by clinical and/or pathological observation. However, when there is no detectable clinical and/or pathological presence of CRC in the subject, the occurrence of CRC in the subject is an increased risk of developing CRC. By assessing CRC in a subject using the method as provided herein, one can also evaluate the effectiveness of a treatment that the subject underwent, when the methylation status of one or more biomarkers in the CRC biomarker profile operable in blood changes over the course of the treatment, for example, from methylated to unmethylated, from higher methylation level to lower methylation level, is indicative of treatment response.

Another aspect of the invention provides a kit for assessing colorectal cancer (CRC) in a subject, and the kit comprises at least one primer pair allowing nucleic acid amplification to produce amplification products specific to methylation status of at least one biomarker of a CRC biomarker profile operable in a blood sample of the subject. The CRC biomarker profile operable in the blood sample comprises PROM1, SARP1, MSF1. Any Methylation of at least one of PROM1, SARP1, MSF1, or any combinations thereof, preferably at least two of, and most preferably all three of PROM1, SARP1, MSF1 is associated with an occurrence of CRC in the subject. In contrast, unmethylated PROM1, SARP1 and MSF1 indicates no occurrence of CRC in the subject.

To detect the methylated PROM1, the kit provides a primer mixture comprising at least one primer pair specific to methylated PROM1; and such primer pair specific to methylated PROM1 is preferably selected from the group consisting of a primer pair having one primer comprising SEQ ID NO. 1 and the other comprising SEQ ID NO. 3; a primer pair having one primer comprising SEQ ID NO. 5 and the other comprising SEQ ID NO. 7; and a primer pair having one primer comprising SEQ ID NO. 9 and the other comprising SEQ ID NO. 11.

To detect the methylated SARP1, the kit provides a primer mixture comprising at least one primer pair specific to methylated specific to methylated SARP1; and such primer pair is preferably selected from the group consisting of a primer pair having one primer comprising SEQ ID NO. 13 and the other comprising SEQ ID NO. 15; a primer pair having one primer comprising SEQ ID NO. 17 and the other comprising SEQ ID NO. 19; a primer pair having one primer comprising SEQ ID NO. 21 and the other comprising SEQ ID NO. 23; and a primer pair having one primer comprising SEQ ID NO. 25 and the other comprising SEQ ID NO. 27.

To detect the methylated MSF1, the kit provides a primer mixture comprising at least one primer pair specific to methylated specific to methylated SARP1; and such primer pair is preferably selected from the group consisting of a primer pair having one primer comprising SEQ ID NO. 29 and the other comprising SEQ ID NO. 31; a primer pair having one primer comprising SEQ ID NO. 33 and the other comprising SEQ ID NO. 35; a primer pair having one primer comprising SEQ ID NO. 37 and the other comprising SEQ ID NO. 39; a primer pair having one primer comprising SEQ ID NO. 41 and the other comprising SEQ ID NO. 45; and a primer pair having one primer comprising SEQ ID NO. 41 and the other comprising SEQ ID NO. 47.

The kit may further or alternatively comprise primer pairs specific to unmethylated PROM1, SARP1, and/or MSF1, which primer pairs are described herein.

Other aspects and iterations of the invention are described in more detail below.

DETAILED DESCRIPTION OF THE INVENTION

This disclosure provides an epigenetic biomarker profile specific for colorectal cancer diagnosis, prognosis and therapy evaluation using blood samples. The invention further provides for a method of detecting a predisposition to, or the incidence of, colorectal cancer in a sample, which method comprises detecting the methylation status of at least one gene selected from a CRC biomarker profile operable in blood samples, which profile comprises PROM1, SARP1 and MSF1. In the method, the methylation status or change in methylation status of at least one selected gene in the profile is detected by determination of the methylation level of the gene. Methylation of at least one gene in the CRC biomarker profile is indicative of the existence of a CRC tumor cell at various stages or a predisposition to colorectal cancer. The method provided herein is convenient, patient-friendly, highly sensitive and specific, and is suited for rapid identification of tumor cell types associated with various stages of colorectal cancer.

I. CRC Biomarker Profile and DNA Methylation

Epigenetic modifications to the genome of cancer cells that do not involve a change in the nucleotide sequence are prevalent. Epigenetic change is mediated by mechanisms other than alterations in the primary nucleotide sequence of a gene. These epigenetic modifications may or may not lead to altered gene expression patterns in the cancerous cells. Epigenetic alteration, change, or modification in gene includes, but is not limited to, DNA methylation, acetylation, phosphorylation, ubiquitylation, sumolyation, histone methylation and acetylation, RNA interference, and dysregulation of DNA binding protein. The epigenetic change in the gene markers of the present invention is generally related to aberrant DNA methylation. By detecting the methylation status of at least one gene in the CRC biomarker profile comprising PROM1, SARP1 and MSF1 in a blood sample, one can diagnose CRC, provide prognosis for a patient diagnosed with CRC, or evaluate therapy effectiveness against CRC in a subject as provided herein.

The occurrence of a CRC, or predisposition thereof, may be indicated by the presence of one or more biomarkers. In some embodiments, a differential level of one or more biomarkers in a sample in comparison to a control may also be used as a diagnosis or prognosis indication. The present invention provides a CRC-associated biomarker profile comprising PROM1, SARP1 and MSF1 genes. Specifically, in one embodiment, the methylation of any one of the biomarkers in the profile is indicative of the existence or predisposition to CRC (an "occurrence of CDC"). In other embodiments, the methylation of any two biomarkers in the profile is indicative of the existence of CRC or predisposition to CRC. Therefore, in one embodiment, the methylation of PROM1 and SARP1 is the CRC diagnostic or prognostic indication. In another embodiment, the methylation of PROM1 and MSF1 is the CRC diagnostic or prognostic indication. In yet another embodiment, the methylation of SARP1 and MSF1 is the CRC diagnostic or prognostic indication. In still another embodiment, the methylation of PROM1, SARP1 and MSF1 is the CRC diagnostic or prognostic indication. The higher the level of methylation in genes selected from the CRC biomarker profile are, the higher the certainty of a CRC diagnosis or prognosis. The methylation status of one or more genes in the CRC biomarker profile comprising PROM1, SARP1 and MSF1 may be determined by PCR, hybridization, sequencing, or any other methods known in the art. Because methylation of a gene often leads to gene silencing, in one embodiment, methods of CRC diagnosis or prognosis using the biomarker profile comprising PROM1, SARP1 and MSF1 comprise assessing the expression level of one or more genes in the profile. Such expression may be assessed by any of a number of methods used currently in the art and yet to be developed.

PROM1 encodes Prominin-1 (PROM1; UniProtKB/Swiss-Prot No. O43490), which is a trans-membrane glycoprotein. PROM1 has been shown to bind cholesterol in cholesterol-containing plasma membrane microdomains. PROM1 is also proposed to play a role in apical plasma membrane organization of epithelial cells. During early retinal development, PROM1 acts as a key regulator of disk morphogenesis. It is known that PROM1 is involved in various forms of retinal dystrophies. PROM1 is involved in regulation of MAPK and Akt signaling pathways. In neuroblastoma cells, PROM1 suppresses cell differentiation such as neurite outgrowth in a RET-dependent manner. The PROM1 gene is located at chromosome 4p15.32.

SARP1 encodes secreted frizzled-related protein 2 (SARP1; UniProtKB/Swiss-Prot No. Q96HF1), which functions as modulators of Wnt signaling through direct interaction with Wnts. They have a role in regulating cell growth and differentiation in specific cell types. SFRP2 may be important for eye retinal development and for myogenesis. The gene encoding SARP1 is located at chromosome 4q31.3.

MSF1 encodes septin-9 (MSF1; UniProtKB/Swiss-Prot No. Q9UHD8), which is a protein involved in cytokinesis and cell cycle control. The gene encoding the MSF1 protein is located at chromosome 17q25 and is a candidate for the ovarian tumor suppressor gene. Mutations in this gene cause hereditary neuralgic amyotrophy, also known as neuritis with brachial predilection. A chromosomal translocation involving this gene on chromosome 17 and the MLL gene on chromosome 11 results in acute myelomonocytic leukemia.

Through numerous screening, testing and assay designing, it was discovered in the present invention that, not only the DNA of the genes in the CRC biomarker profile remains intact, rather than degraded, in a blood sample, but the methylation status of these genes in blood is indicative of CRC or a predisposition thereof with high sensitivity and specificity. Therefore, one aspect of the present invention provides that the methylation status of at least one of the selected biomarkers in the profile is useful for determining CRC occurrence including diagnosis, prognosis and theragnosis (i.e., evaluation of treatment response). Specifically, the presence of at least one methylated gene selected from the profile is indicative of CRC diagnosis and prognosis. Further, it seems that the level of the methylation of a gene marker selected from the profile is associated with the stage of the CRC. Once CRC or its predisposition associated biomarkers are identified, various methods may be used to screen samples to specifically and selectively detect the methylation status of the biomarker to make diagnosis, prognosis or therapy evaluation. Some exemplary methods are detailed below.

"Methylation status", as used in the present invention, refers to the presence or absence of a methylated cytosine residue in one or more CpG dinucleotides within the nucleic acid or gene of interest. In some embodiments, methylation status is depicted by measuring the level of methylation, for which various quantification methods are known in the art. CpG islands are identifiable through a range of techniques, including sequencing and in silico predictive methods. CpG islands can be found in multiple regions of a nucleic acid sequence including upstream of coding sequences in a regulatory region including a promoter region, in the coding regions (e.g. exons), downstream of coding regions in, for example, enhancer regions, and in introns. All of these regions can be assessed to determine their methylation status, as appropriate. When the CpG distribution in the promoter region is rather scarce, levels of methylation may be assessed in the intron and/or exon regions. The region for assessment may be a region that comprises both intron and exon sequences and thus overlaps both regions. In one embodiment, the CpG islands under investigation are in the promoter region which begins just upstream of a promoter and extends downstream into the transcribed region. In another embodiment, the CpG islands under investigation surround the 5' region of the coding region of the gene as well as the 3' region of the coding region. Thus, in certain embodiments, the methylation status of the gene is assessed by determining levels of methylation in the promoter, intron, exon1 and/or exon2 region of the gene. A "promoter" is a region upstream from the transcription start site (TSS), extending between approximately 10 Kb, 4 Kb, 3 Kb, 1 Kb, 500 bp, 300 bp, 150 bp, or any range thereof, from the TSS. More specifically, the methods of the invention investigate the methylation status, of the relevant gene or genes around the TSS.

What makes it more difficult and complex to develop a useful marker detectable in a blood sample is that the genomic DNA in blood is by and large degraded by DNase. Some genomic regions are more susceptible to DNase. For example, promoters, enhancers, suppressors, insulators, and locus control regions all have been shown to be associated with DNase hypersensitive sites (DHS). In addition, there is an enrichment of DHSs detected within the 2 kb upstream and downstream of genes, and in first exons, first introns, CpG islands and highly conserved regions. Therefore, if a gene, or a part thereof, is in one of those degradable regions, it is not a reliable indication as to the presence or absence of a biomarker in a blood sample. Moreover, to select an amplicon (amplification product) having methylation status associated with CRC, CRC staging, and/or CRC predisposition, within a gene sequence, for a PCR-based methylation assay, it demands even more stringent validation for reliability, reproducibility, sensitivity and specificity.

The term "sample" or "biological sample" is used in its broadest sense. Depending upon the embodiment of the invention, for example, a sample may comprise a bodily fluid including whole blood, serum, plasma, urine, stool, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a colorectal tissue; a colorectal tissue print or any other colorectal material isolated in whole or in part from a living subject. In some embodiment, biological samples may also include sections of colorectal tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient colorectal tissues. A biological sample is typically obtained from a eukaryotic organism, most preferably a mammal such as a primate e.g., human. Preferably, the biological sample in the present invention is whole blood, plasma, or serum. Applying the biomarker profile and the method of use, as provided herein, to a biological sample other than blood, is also understandably within the scope of this invention.

A biological sample for use is obtained in methods described in this invention. Most often, this will be done by removing a sample from a subject, but can also be accomplished by using previously isolated samples (e.g., isolated by another person, at another time, and/or for another purpose), or by performing the methods of the invention in vivo. Archival colorectal tissues, blood or serum, having treatment or outcome history, will be particularly useful.

The term "subject" is used in its broadest sense. In a preferred embodiment, the subject is a mammal. Non-limiting examples of mammals include humans. Preferably, a subject includes any human capable of developing colorectal cancer including those who are suspected of having colorectal cancer, who have been diagnosed with colorectal cancer, or who have a family history of colorectal cancer. Methods of identifying subjects suspected of having cancer include but are not limited to: physical examination, family medical history, subject medical history, endometrial biopsy, or a number of imaging technologies.

Samples may be collected by any and all methods now known or yet to be disclosed to collect bodily fluids in such a way as to preserve biological material such as DNA, or more specifically, methylated DNA for analysis.

II. Methods for Determining Methylation Status of a Selected Biomarker

The present invention provides for a method of diagnosing colorectal cancer or predisposition thereof comprising detecting methylation of at least one gene selected from the CRC biomarker profile comprising PROM1, SARP1 and MSF1, wherein the methylation of the at least one gene in a blood sample of a subject is indicative of CRC or its predisposition. Thus, in certain embodiments, the methods of the invention may comprise, consist essentially of or consist of determining the methylation status of the gene or gene combinations of the CRC biomarker profile. The methylation status of one or more genes in the CRC biomarker profile may be compared with that of a control blood sample from a healthy individual who also does not have CRC predisposition. Positive controls may be employed as required. In specific embodiments, the methylation status is determined using multiplex methylation specific PCR. In certain embodiments, the methylation status of a gene in the CRC biomarker profile is represented by the methylation at the gene promoter region. In other embodiments, the methylation status of a gene in the CRC biomarker profile is represented by the methylation at a selected CpG island. In one embodiment, the method of assessing colorectal cancer or predisposition to colorectal cancer comprises detecting methylation of at least two genes in the CRC biomarker profile comprising PROM1, SARP1 and MSF1. Therefore, in one embodiment, the method comprises detecting methylation of PROM1 and SARP1. In another embodiment, the method comprises detecting methylation of PROM1 and MSF1. In yet another embodiment, the method comprises detecting methylation of SARP1 and MSF1. In still another embodiment, the method of detecting colorectal cancer or predisposition to colorectal cancer comprises detecting methylation of PROM1, SARP1 and MSF1.

There are a variety of techniques using distinct approaches for assessing methylation status, such as hyper-methylation or hypo-methylation, or methylation change, and/or measuring the level of methylation. Bisulfite sequencing, MSP (methylation specific PCR), MS-SnuPE (methylation-sensitive single nucleotide primer extension), COBRA (Combined bisulfite restriction analysis), Methyl-Light (a sodium-bisulfite-dependent quantitative real-time PCR), QMSP (Quantitative methylation-specific PCR), MALDI-TOF MS (Matrix assisted laser desorption/ionisation, time-of-flight mass spectrometry), and methylation pyrosequencing are all being used to qualitatively or quantitatively analyze locus- and often multi-locus specific methylation in a variety of developmental samples and tumors. Other exemplary techniques include, but are not limited to, melting curve methylation-specific PCR, MLPA (multiplex ligation-dependent probe amplification) with or without bisulfite treatment, QAMA (quantitative analysis of methylated alleles), MSRE-qPCR (Methyl Sensitive Restriction Enzyme-based quantitative PCR), ConLight-MSP (conversion-specific detection of DNA methylation using quantitative PCR), BS-MSP (bisulphite conversion-specific methylation-specific PCR), MS-SSCA (methylation-sensitive single-strand conformation analysis), McCOBRA (Melting curve combined bisulphite restriction analysis), ERMA (enzymatic regional methylation assay). Other techniques also include quantitative PCR sequencing and oligonucleotide-based microarray systems, such as Meth-DOP-PCR, a method for methylation profiling of trace amounts of DNA extracted from bodily fluids, and MALDI-TOF-MS array analysis.

Some of the above methylation-specific PCR, sequencing or array techniques include the use of endonucleases that preferentially cleave non-methylated relative to methylated recognition sites, or vice versa. Differences in cleavage pattern are indicative for the presence or absence of a methylated CpG dinucleotide. The cleavage patterns can in turn be detected directly because of the modified product, or after a further reaction which creates products which are distinguishable for altered size or charge, which can be detected by methods including, but not limited to, electrophoresis, chromatography, and mass spectrometry.

Alternatively, the identification of methylated CpG dinucleotides may utilize the ability of the methyl binding domain (MBD) of the MeCP2 MBP, MBP2, MBP4, poly-MBD proteins or antibodies to selectively bind to methylated DNA sequences. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulfite ions. For example, treating DNA samples with sodium bisulfite converts unmethylated cytosine to uracil, while methylated cytosines are maintained, and the resulting uracil has the base pairing behavior of thymidine which differs from cytosine base pairing behavior. This conversion finally results in detectable change in the sequence of the original DNA.

Some techniques use primers for assessing the methylation status at CpG dinucleotides. Primers may be designed such that they do not contain any potential sites of DNA methylation, whereas the detectable sequence variations at sites of differential methylation are located between the two primers. Such primers can be used in bisulphite genomic sequencing, COBRA, Ms-SnuPE and several other techniques. Alternatively, primers may be designed that hybridize specifically with either the methylated or unmethylated target sequence. After hybridization, an amplification reaction can be performed and amplification products assayed using any detection system known in the art. The presence of an amplification product indicates that the primer has hybridized to its target sequence in a sample. The specificity of the primer indicates whether the DNA had been modified or not, which in turn indicates whether the DNA had been methylated or not. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats.

A further way to distinguish between methylated and unmethylated nucleic acid is to use oligonucleotide probes. Such probes may hybridize directly to modified nucleic acid with or without amplification. Probe-based assays exploit the oligonucleotide hybridization to specific sequences and subsequent detection of the hybrid. Oligonucleotide probes may be labeled using any detection system known in the art. These include but are not limited to fluorescent moieties, radioisotope labeled moieties, bioluminescent moieties, luminescent moieties, chemi-luminescent moieties, enzymes, substrates, receptors, or ligands. For example, MSP (methylation-specific PCR) approach amplifies DNA using primer pairs designed to distinguish methylated from unmethylated DNA by taking advantage of sequence differences as a result of sodium-bisulphite treatment. For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA. Amplification using a DNA polymerase and a second primer yields amplification products which can be readily observed, which in turn indicates whether the DNA had been methylated or not. Whereas PCR is a preferred amplification method, variants on this basic technique such as nested PCR, multiplex PCR, ligase chain reaction (LCR), self-sustained sequence replication (3SR), nucleic acid sequence based amplification (NASBA), strand displacement amplification (SDA), amplification with Qβ replicase, are also included within the scope of the invention. In the present invention, a preferred embodiment for assessing the methylation status of the relevant gene requires amplification to yield amplification products.

With PCR, it is possible to amplify a single copy of a specific target sequence in a sample to a level detectable by several different methodologies. The presence of amplification products may be assessed directly using methods well known in the art. They may be visualized on a suitable gel, such as an agarose or polyacrylamide gel. Detection may involve the binding of specific dyes, such as ethidium bromide, which intercalate into double-stranded DNA and visualization of the DNA bands under a UV illuminator for example. Another means for detecting amplification products comprises fluorescence or energy transfer that can be measured to determine the presence of the methylated DNA. Alternatively, in some embodiment, hybridization with oligonucleotide probes that are labeled facilitates the detection of the amplification products. For example, labeled probes release their fluorescent tags during the extension phase so that the fluorescence level may be detected or measured. Generally, probes are complimentary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent) stain, enzyme, or nonradioactive metal. Specific examples include, but are not limited to: fluorescein, biotin, digoxigenin, alkaline phosphatese, biotin, streptavidin, $^{3}H$, $^{14}C$, $^{32}P$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra acetic acid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Another application of the MSP technique is called real-time quantitative MSP (QMSP), which permits reliable quantification of methylated DNA in real time or at end point. Real-time methods are generally based on the continuous optical monitoring of an amplification procedure and utilize fluorescently labeled reagents whose incorporation in a product can be quantified and whose quantification is indicative of copy number of that sequence in the template. One such reagent is a fluorescent dye, SYBR Green I, that preferentially binds double-stranded DNA and whose fluorescence is greatly enhanced by binding of double-stranded DNA. Alternatively, labeled primers and/or labeled probes can be used for quantification. They represent a specific application of the well-known and commercially available real-time amplification techniques such as TAQMAN®, MOLECULAR BEACONS®, AMPLIFLUOR® and SCORPION®, DzyNA®, Plexor™ etc. In the real-time PCR systems, it is possible to monitor the PCR reaction during the exponential phase where the first significant increase in the amount of PCR product correlates to the initial amount of target template.

Real-Time PCR detects the accumulation of an amplicon (amplification product) during the reaction. When the analysis is to confirm whether the target DNA is present in the sample or not, end-point verification can be carried out after the amplification reaction has finished. In the present invention, such analysis is preferred to detect a predisposition to, or the incidence of, colorectal cancer in a patient. End-point PCR fluorescence detection techniques may employ the same approaches as widely used for Real Time PCR. For example, instruments such as "Gene" detector ("Gene-Machine") allow the measurement of fluorescence directly in PCR tubes (Bioron GmbH, Ludwigshafen, German). The quantitation of methylation using real-time PCR may be on an absolute basis, or may be relative to a constitutively methylated DNA standard, or may be relative to an unmethylated DNA standard. Methylation status may be determined by using the ratio between the signal of the marker under investigation and the signal of a reference gene where methylation status is known, or by using the ratio between the methylated marker and the sum of the methylated and the non-methylated marker. Alternatively, absolute copy number of the methylated marker gene can be determined.

One aspect of the invention provides a multiplex PCR assay to determine the methylation status of more than one gene marker in the profile. Multiplex PCR is a technique for amplification of multiple targets in a single PCR experiment. In a multiplexing assay, more than one target sequence can be amplified by using multiple primer pairs in a reaction mixture. As an extension to the practical use of PCR, this technique has the potential to produce considerable savings in time and effort within the laboratory without compromising on the utility of the experiment. Aside from differential methylation detection required for these primers, design of specific primer sets is essential for a successful multiplex reaction, and the factors to be considered include primer length, melting temperature, specificity, and primer dimerization.

In some forms of multiplex PCR assays, relative quantification is often used to determine the changes in the methylation levels of a gene across multiple samples, and describe the level of methylation in reference to the levels of an internal control sample. The control sample may be co-amplified in the same mixture for a multiplex assay or may be amplified in a separate mixture. Suitable controls may need to be incorporated in order to ensure the method chosen is working correctly and reliably. Suitable controls may include assessing the methylation status of a gene known to be methylated. A positive control can also be included to help ensure that false negative results are not obtained. The gene may be one which is known to be methylated in the sample under investigation or it may have been artificially methylated.

In certain embodiments, MSP (Methylation-specific-PCR) primers are utilized in the methods of the invention. In some embodiment, multiplex methylation-specific-real-time-PCR is used when the methylation status of more than one gene is analyzed simultaneously in a sample. The present invention provides exemplary primers useful in MSP to determine the methylation status of the genes in the CRC biomarker profile, as set forth in Table 1 below. These primers may comprise, consist essentially of or consist any of the nucleotide sequences set forth in the table. In Table 1, primers designated as "methylated" preferably are designed to bind to fully methylated target region in the genomic sequences of the gene in the CRC biomarker profile, and produce amplification products specific to a methylated biomarker or a part thereof; whereas primers designated as "unmethylated" preferably are designed to bind to the same but unmethylated target region in the genomic sequences of the gene in the CRC biomarker profile, thereby produce amplification products specific to a unmethylated biomarker or a part thereof. Therefore, the amount of amplicons by primers designated as "methylated" or by primers designated as "unmethylated" provides the measurement of the methylation status of a target region of a selected gene in a given sample.

TABLE 1

MSP Primers for Genes in the CRC Biomarker Profile

| Gene | Forward (5'-3') $^{\Delta}$Methylated/*Unmethylated | Seq ID NO. | Reverse (5'-3') $^{\Delta}$Methylated/*Unmethylated | Seq ID NO. |
|---|---|---|---|---|
| PROM1 | $^{\Delta}$TTTTGATTTTTAGTGTTGCG | 1 | $^{\Delta}$AATTTAATCTATCCCTAC | 3 |
| | *TTTTTGATTTTTAGTGTTGTG | 2 | *AATTTAATCTATCCCTAC | 4 |
| | $^{\Delta}$AGTTTTTTAGTTAGATTTCG | 5 | $^{\Delta}$AACAAAATAAACTCACAAAA | 7 |
| | *GAGTTTTTTAGTTAGATTTTG | 6 | *AACAAAATAAACTCACAAAA | 8 |
| | $^{\Delta}$GGTATATTAGTTAGTTCG | 9 | $^{\Delta}$AAAACAAAAAATATCCCCGA | 11 |
| | *GGGTATATTAGTTAGTTTG | 10 | *AAAACAAAAAATATCCCCAA | 12 |
| SARP1 | $^{\Delta}$CGGAGTTTTTCGGAGTTGCG | 13 | $^{\Delta}$ACTAAAACGCGAAAAAACGA | 15 |
| | *TTGGAGTTTTTTGGAGTTGTG | 14 | *GACTAAAACACAAAAAAACAA | 16 |
| | $^{\Delta}$CGGTTTATTTTGTTTTTTCG | 17 | $^{\Delta}$CGAAAAAACAACGCGAACGA | 19 |
| | *ATGGTTTATTTTGTTTTTTTG | 18 | *CCAAAAAAACAACACAAACAA | 20 |
| | $^{\Delta}$TTTTTCGGGGTTTCGAGTCG | 21 | $^{\Delta}$TCGTAAACGCGCGACCCCGA | 23 |
| | *GTTTTTTGGGGTTTTGAGTTG | 22 | *CATCATAAACACACAACCCCAA | 24 |
| | $^{\Delta}$GCGGGTTCGGGATAAGTTCG | 25 | $^{\Delta}$CAAACAACAATACGAAACGA | 27 |
| | *GTGGGTTTGGGATAAGTTTG | 26 | *CCCAAACAACAATACAAAACAA | 28 |
| MSF1 | $^{\Delta}$GGAGGGGGGCGTTTCGGTCG | 29 | $^{\Delta}$AACTAAAACCCGAATAACCG | 31 |
| | *AGGAGGGGGGTGTTTTGGTTG | 30 | *AAACTAAAACCCAAATAACCA | 32 |
| | $^{\Delta}$TTTTGGGCGCGGGTTAGGCG | 33 | $^{\Delta}$CTAAACACACGACCGAAACG | 35 |
| | *TTTTTTGGGTGTGGGTTAGGTG | 34 | *CCTAAACACACAACCAAAACAC | 36 |
| | $^{\Delta}$TGAGGTCGCGTTTTTCGTCG | 37 | $^{\Delta}$AATCCTAAACACACGACCGA | 39 |
| | *GTTGAGGTTGTGTTTTTTGTTG | 38 | *ACAATCCTAAACACACAACCAA | 40 |
| | $^{\Delta}$TGGTCGTAGCGGGGCGTTCG | 41 | $^{\Delta}$CCCGCCTAACCCGCGC | 43 |
| | *ATTTGGTTGTAGTGGGGTGTTTG | 42 | *TCCCCACCTAACCCACAC | 44 |
| | $^{\Delta}$ATTTTTGTAGGCGTAGAGCG | 45 | $^{\Delta}$TCCCCTTCCCCGAACGC | 47 |
| | *ATTTTTGTAGGTGTAGAGTG | 46 | *CTCCCCTTCCCCAAACAC | 48 |

Further characteristics of these primers, such as performance evaluated by assay specificity and sensitivity, are summarized in the experimental part. It is noted that variants of these sequences may be utilized in the present invention. In particular, additional flanking sequences may be added, for example to improve binding specificity, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers set forth herein.

As used herein, "sequence identity" or "identity" in the context of two nucleic acid sequences includes reference to the nucleic acid bases in the two sequences which are the same when aligned for maximum correspondence over a specified comparison window. As used herein, "percentage of sequence identity" means the value determined by comparing two optimally aligned sequences over a comparison window, wherein the portion of the polynucleotide sequence in the comparison window may comprise additions or deletions (i. e., gaps) between the two, or more optimally aligned sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The primers may incorporate synthetic nucleotide analogues as appropriate or may be DNA, RNA or PNA based for example, or mixtures thereof. Similarly alternative fluorescent donor and acceptor moieties/FRET pairs may be utilized as appropriate. In addition to being labeled with the fluorescent donor and acceptor moieties, the primers may include modified oligonucleotides and other appending groups and labels provided that the functionality as a primer in the methods of the invention is not compromised.

To calculate the level of methylation based on the copies of a methylated target sequence in relation to an adequate reference sequence, various mathematical models are established. Calculations are based on the comparison of the distinct cycle determined by various methods, e.g., crossing points (Cp) and cycle threshold values (Ct) at a constant level of fluorescence; or Cp acquisition according to established mathematic algorithms.

The algorithm for Ct values in Real Time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. Cp value represents the cycle at which the increase of fluorescence is highest and where the logarithmic phase of a PCR begins. The LightCycler® 480 Software (Roche Applied Science, Penzberg, Germany) calculates the second derivatives of entire amplification curves and determines where this value is at its maximum. The second-derivative algorithm enables data collection when fluorescence is relatively low, and the data so obtained are more reliable and reproducible.

Therefore, the methylation status of one or more biomarkers of the profile may be determined by one or more of the methods described above. In one embodiment, the presence of the PCR or Real Time-PCR methylated products in an assay may indicate the presence of CRC incidence or predisposition. In one embodiment, the PCR or Real Time- PCR products may be further identified or differentiated by hybridization undergoing simultaneously or subsequently with the PCR reactions. In another embodiment, the PCR or Real Time-PCR products may be sequenced to ascertain the existence of a particular allele with methylation indicative of the CRC or predisposition thereof.

III Kits.

Still another aspect of the invention encompasses kits for identifying an occurrence of CRC, including diagnosing CRC or identifying predisposition thereof via identifying the methylation status of genes selected from the CRC biomarker profile comprising PROM1, SARP1, and MSF1. In one embodiment, the kits comprise primer sets for detecting methylation status of at least one biomarker selected from the profile. In another embodiment, the kits comprise primer sets for detecting methylation status of at least two biomarkers selected from the profile. In yet another embodiment, the kits comprise primer sets for detecting methylation status of at least three biomarkers selected from the profile. As provided in Table 1 above, primers comprising SEQ ID NOs: 1, 2, 3, and 4, or primers comprising SEQ ID NOs: 5, 6, 7, and 8, or primers comprising SEQ ID NOs: 9, 10, 11, and 12 can be included in a kit for detecting at least the methylation status of PROM1 using methylation specific PCR methods. Further, primers comprising SEQ ID NOs: 13, 14, 15, and 16, or primers comprising SEQ ID NOs: 17, 18, 19, and 20, or primers comprising SEQ ID NOs: 21, 22, 23, and 24, or primers comprising SEQ ID NOs: 25, 26, 27, and 28 can be included in a kit for detecting at least the methylation status of SARP1 using methylation specific PCR methods. In addition, primers comprising SEQ ID NOs: 29, 30, 31, and 32, or primers comprising SEQ ID NOs: 33, 34, 35, and 36, or primers comprising SEQ ID NOs: 37, 38, 39, and 40, or primers comprising SEQ ID NOs: 41, 42, 43, and 44 can be included in a kit for detecting at least the methylation status of MSF1 using methylation specific PCR methods.

The kits for diagnosing CRC or predisposition thereof via identifying methylation status of genes selected from the CRC biomarker profile comprising PROM1, SARP1, and MSF1 may further comprise one or more of the following: nucleic acid extraction reagents, controls, disposable cartridges, labeling reagents, enzymes, PCR amplification reagents, or one or more other reagents that facilitate methylation specific PCR.

In another embodiment, the kit may further comprise a label that can be used to label the primer oligonucleotide. A label may be any substance capable of aiding a machine, detector, sensor, device, or enhanced or unenhanced human eye, in differentiating a sample that displays hyper-versus hypo-methylation from a control sample for comparison. Examples of labels include, but are not limited to: a radioactive isotope or chelate thereof, a dye (fluorescent or nonfluorescent) stain, enzyme, or nonradioactive metal. Specific examples include, but are not limited to: fluorescein, biotin, digoxigenin, alkaline phosphatase, biotin, streptavidin, $^{3}H$, $^{14}C$, $^{32}P$, $^{35}S$, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralen derivatives, haptens, cyanines, acridines, fluorescent rhodol derivatives, cholesterol derivatives; ethylene diamine tetra-acetic acid ("EDTA") and derivatives thereof, or any other compound that signals the presence of the labeled nucleic acid. In one embodiment of the invention, the label includes one or more dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ.

In yet another embodiment, the primers in the kit may have been labeled, and can be applied without a labeling process in PCR, sequencing reaction, or binding to a solid substrate such as oligonucleotide array. A kit for diagnosing CRC or predisposition thereof via identifying methylation status of genes selected from the CRC biomarker profile comprising PROM1, SARP1, and MSF1 may also comprise instructions for use. In one embodiment, the kit may further comprise an indication that links the output of the assays provided by the kit to a particular result. For example, an indication may provide guidance to associate the presence of one or more methylated genes selected from the CRC biomarker profile to a CRC diagnosis or prognosis. For example, an indication may further provide guidance to associate the presence of one or more methylated genes selected from the CRC biomarker profile to a level of confidence for a CRC diagnosis or prognosis. The indication may contain a standard curve configured to quantify the methylation status of a gene biomarker. The output of the assay may be in the form of a particular sequence, a particular genotype, a particular Ct level in a real-time quantitative PCR reaction, a level of fluorescence or radioactive decay, a value derived from a standard curve, or from a positive or negative control, or any combination of these and other outputs. The indication may be printed as a written material that may be included in the kit, or it may be posted on the Internet, or embedded in a software package. The written material may include graphical depictions of results such as a photomicrograph or amplification plot.

The kits for diagnosing CRC or predisposition thereof via identifying methylation status of genes selected from the CRC biomarker profile comprising PROM1, SARP1, and MSF1 may further comprise a device used to collect the sample. Such devices may include but need not be limited to: swabs, needles, blood collection tubes, wipes, or any other apparatus that may be used to collect a biological sample from a patient or from the environment now known or yet to be disclosed. Preferably, the kits comprise a device used to collect blood samples.

Although the invention described herein is susceptible to various modifications and alternative iterations, specific embodiments thereof have been described in greater detail above. It should be understood, however, that the detailed description of the CRC biomarker profile and the use thereof is not intended to limit the invention to the specific embodiments disclosed. Rather, it should be understood that the invention is intended to cover all modifications, equivalents, and alternatives falling within the spirit and scope of the invention as defined by the claim language.

EXAMPLES

The following examples illustrate certain aspects of the invention without limiting the scope of the invention.

Example 1—Methods and Materials

Patient Selection and Clinical Specimens:

All subjects were diagnosed as having CRC by pathological analysis. Clinical and pathological data were obtained from the relevant patient records and are summarized in Table 2. The CRC tissue analyzed was obtained from surgical resections including colonoscopy, fresh-frozen, and stored at −80° C. Blood was drawn and serum samples were obtained from healthy individuals and CRC patients before, or a minimum of one week, after colonoscopy. The clinical diagnosis of CRC was confirmed by histologic analysis, and colonoscopy examinations confirmed that healthy individuals have no colon-related disease. Samples were archives dating from 2010-2012 at the First Hospital of China Medical University. Ethical approval for the study was obtained from the ethics committee of the First Hospital of China Medical University. Ethical approval was granted for retrospective analysis of tissue specimens.

TABLE 2

Disease and stage distribution of patient samples

| | Total | Male | Female | Median age (range) |
|---|---|---|---|---|
| Colorectal cancer | 128 | 79 | 49 | 64(40-87) |
| Stage I | 20 | 13 | 7 | 65(50-83) |
| Stage II | 58 | 32 | 26 | 66(40-87) |
| Stage III | 43 | 29 | 14 | 61(41-76) |
| Stage IV | 7 | 5 | 2 | 65(51-75) |
| Control | 92 | 41 | 51 | 55(41-82) |
| Total | 220 | | | |

Blood Sample Preparation:

Collect 2 ml of blood in standard lab tiger-top SST (serum separator tube) tube. Allow tubes with samples to sit upright at room temperature for a minimum of 30 minutes and a maximum of 2 hours. Separate the clot by centrifugation at room temperature or 4° C. at 1300×g for 15 minutes. The serum was removed and transferred to a cryovial. Immediately snap freeze the samples by placing the cryovial in dry ice and then store the vial in the −80° C. freezer, or proceed to DNA extraction of experiment protocol.

Serum DNA Extraction:

Total DNA was extracted using Qiagen's QIAamp DNA Blood Kit according to the manufacturer's instructions (Qiagen, Valencia, Calif.). Briefly, 200 μl serum was used to start with the extraction. Follow the manufacturer's manual for the procedure. After the DNA is extracted, continue bisulfite conversion assay or store at −80° C. for longer storage.

Bisulfite Modification and Methylation Specific Real-Time PCR:

Genomic DNA from cell lines (500 ng), as control, and blood specimens (50 ng) were bisulfite modified using the Qiagen's EpiTect Bisulfite kit (Qiagen, Gaithersburg, Md.). The CpGenome Universal Methylated DNA and Unmethylated DNAs (Chemicon International, Temecula, Calif.) were used as positive controls. Promoter hypermethylation was analyzed by methylation specific PCR (MSP) in subjects using the Qiagen HotStar Taq PCR kit and Roche 480 Thermocycler (Roche, Indianapolis, Ind.). PCR primer sets complementary to both modified, methylated DNA and modified, unmethylated DNA were designed for all genes (Table 3). Forty-five cycles of PCR were performed (95° C. 15 minutes for hot start; 45 cycles of 95° C. 30 seconds, 59° C. 30 seconds and 72° C. 60 seconds). Beta-actin was used as an internal control.

Statistical Analysis:

The study was run in a batch mode, using positive and negative controls for each DNA extraction. Data collection included total genomic DNA recovery following extraction and real-time PCR measurements. All PCR results were confirmed by visual inspection of the PCR curves. Each PCR run included calibrator samples and at least one no-template control sample. DNA concentration (methylated and unmethylated DNA of the markers) was determined from calibration curves by linear regression of crossing point values using the second derivative method. For clinical samples, serum samples from 128 cancer cases, primarily stage I-IV, and 92 non-cancer controls were processed and analyzed. The resulting data were analyzed using multiple algorithms to calculate optimized sensitivity and specificity values.

Example 2—Marker Selection

In summary, more than 800 cancer markers commonly referenced from the GenBank, NCBI and Sanger cancer databases were assessed. The candidate marker selection for the CRC biomarker profile, as disclosed herein, was based on in-house criteria developed in the discovery, which include, but are not limited to, the frequency of cancerous alleles, genome-wide biomarker discovery and association scoring system, as well as multiple independent identification experiments conducted during the discovery process. To resolve the problems facing the CRC diagnosis, and to make the test simple and effective, markers performing well in body fluid, such as blood, were preferentially selected. However, genomic DNA in blood is by and large degraded by DNase. Some genomic regions are more susceptible to DNase. For example, promoters, enhancers, suppressors, insulators, and locus control regions all have been shown to be associated with DNase hypersensitive sites (DHS). In addition, there is an enrichment of DHSs detected within the 2 kb upstream and downstream of genes, and in first exons, first introns, CpG islands and highly conserved regions. Therefore, if a gene, or a part thereof, is in one of those degradable regions, it is not a reliable indicator as to the presence of absence of a biomarker in a blood sample. Moreover, selecting an amplicon specific to methylation status associated with CRC, CRC staging, and/or CRC predisposition, within a gene marker for a PCR-based methylation assay, demands even more stringent validation for reliability, reproducibility, sensitivity and specificity. PROM1, SARP1, and MSF1 were selected following the screening. The selected markers as disclosed in this application were all validated in blood samples to ensure their presence and accuracy. Multiplexing PCR was developed to measure each of the selected CRC markers, either alone or in combination with one or more of the other markers. Each of the assays was tested for its sensitivity and specificity.

Example 3—Assay Development and Validation

The selected markers as disclosed in this application were all validated in blood samples to ensure their presence and accuracy. Multiplexing PCR was developed to measure each of the selected CRC markers using blood samples from the patients as shown in Table 2. The positivity and specificity rate for one, or two, or three of the markers are provided and compared in Table 3, based on clinical data of the samples, the control and testing group in the assays. All of the assays have been shown to have satisfying sensitivity and specificity, ranging between about 71% to about 92%, and 69% to 95%, respectively. Generally, all assays having two-biomarker combination performed significantly better than any single biomarker based assay. PROM1/MSF1 has the highest sensitivity and specificity among all the two-marker combinations, and is comparable to the 3-marker combination assay. The assay based on all three biomarkers provides the best performance of all assays based on the CRC biomarker profile as provided, with sensitivity as high as 92% and specificity as high as 95% (see Table 3).

TABLE 3

Assays Based on One or More Biomarkers in The Profile

| | PROM1 | SARP1 | MSF1 | PROM1/ SARP1 | PROM1/ MSF1 | SARP1/ MSF1 | PROM1/SARP1/ MSF1 |
|---|---|---|---|---|---|---|---|
| Sensitity[1] | 71% | 76% | 78% | 86% | 91% | 89% | 92% |
| Specificity[2] | 69% | 78% | 76% | 91% | 94% | 94% | 95% |

[1]Data were obtained from 128 CRC patients and 92 healthy controls.

[2]Data were obtained from 139 patients with 8 other major solid tumors.

The distribution of the samples that were tested positive using the assay with three-marker combination among different CRC stages is shown in Table 4.

TABLE 4

Assay Results from the Assay Using a Three-Marker Combination

| | Positive/tested | % Positive |
|---|---|---|
| Colorectal cancer | 118/128 | 92 |
| Stage I | 17/20 | 85 |
| Stage II | 55/58 | 95 |
| Stage III | 39/43 | 91 |
| Stage IV | 7/7 | 100 |
| Control | 5/92 | 5(95) |

As shown in Table 4, the assay using any of the three biomarkers can identify CRC in all stages, including the early stage I. Further, the assay result for each of the stage has discernible difference in the methylation level of one or more genes in the biomarker profile, which can be further used for CRC staging. Most surprisingly, the assay also identified five positives in the control group, which were considered healthy based on clinical data. Among the five healthy subjects who had shown positive results based on the assay, two were diagnosed with CRC six and nine months after the tests, respectively. This suggests that the assay as disclosed herein can be used for early diagnosis even before cancer cells form and detectable clinically. Physicians are following up with the other 3 test positives for their potential higher risk of developing CRC, which result would be useful to further confirm the power of the assay for CRC early diagnosis and prognosis. Under the assays comprising one or more of the genes in the biomarker profile, healthy individuals with no CRC predisposition do not have methylated PROM1, SARP1, or MSF1 in their blood samples.

Furthermore, the test has been used in assessing other major cancers, and observed 7 of 139 positive patients, or a specificity of 95%, highest among other reported methods. One skilled in the art would readily appreciate that the methods, compositions, and products, described herein, are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

What is claimed is:

1. A method of assessing biomarkers within a blood sample from a subject comprising:
a) obtaining a blood sample comprising DNA from the subject;
b) treating the DNA with bisulfite;
c) amplifying specific methylation regions of at least two biomarkers within the treated DNA, wherein the at least two biomarkers are selected from the group consisting of: PROM1, SARP1 and MSF1, and
wherein amplifying PROM1 comprises the use of:
at least one methylation primer pair selected from the group consisting of:
1) a methylation primer comprising the nucleotide sequence of SEQ ID NO: 1 and a methylation primer comprising the nucleotide sequence of SEQ ID NO: 3;
2) a methylation primer comprising the nucleotide sequence of SEQ ID NO: 5 and a methylation primer comprising the nucleotide sequence of SEQ ID NO: 7; and
3) a methylation primer comprising the nucleotide sequence of SEQ ID NO: 9 and a methylation primer comprising the nucleotide sequence of SEQ ID NO: 11, and
at least one unmethylation primer pair selected from the group consisting of:
1) an unmethylation primer comprising the nucleotide sequence of SEQ ID NO: 2 and an unmethylation primer comprising the nucleotide sequence of SEQ ID NO: 4;
2) an unmethylation primer comprising the nucleotide sequence of SEQ ID NO: 6 and an unmethylation primer comprising the nucleotide sequence of SEQ ID NO: 8; and
3) an unmethylation primer comprising the nucleotide sequence of SEQ ID NO: 10 and an unmethylation primer comprising the nucleotide sequence of SEQ ID NO: 12, and
wherein amplifying SARP1 comprises the use of:
at least one methylation primer pair selected from the group consisting of:
1) a methylation primer comprising the nucleotide sequence of SEQ ID NO: 13 and a methylation primer comprising the nucleotide sequence of SEQ ID NO: 15;
2) a methylation primer comprising the nucleotide sequence of SEQ ID NO: 17 and a methylation primer comprising the nucleotide sequence of SEQ ID NO: 19;
3) a methylation primer comprising the nucleotide sequence of SEQ ID NO: 21 and a methylation primer comprising the nucleotide sequence of SEQ ID NO: 23; and
4) a methylation primer comprising the nucleotide sequence of SEQ ID NO: 25 and a methylation primer comprising the nucleotide sequence of SEQ ID NO: 27, and
at least one unmethylation primer pair selected from the group consisting of:
1) an unmethylation primer comprising the nucleotide sequence of SEQ ID NO: 14 and an unmethylation primer comprising the nucleotide sequence of SEQ ID NO: 16;
2) an unmethylation primer comprising the nucleotide sequence of SEQ ID NO: 18 and an unmethylation primer comprising the nucleotide sequence of SEQ ID NO: 20;
3) an unmethylation primer comprising the nucleotide sequence of SEQ ID NO: 22 and an unmethylation primer comprising the nucleotide sequence of SEQ ID NO: 24; and
4) an unmethylation primer comprising the nucleotide sequence of SEQ ID NO: 26 and an unmethylation primer comprising the nucleotide sequence of SEQ ID NO: 28, and
wherein amplifying MSF1 comprises the use of:
at least one methylation primer pair selected from the group consisting of:
1) a methylation primer comprising the nucleotide sequence of SEQ ID NO: 29 and a methylation primer comprising the nucleotide sequence of SEQ ID NO: 31;
2) a methylation primer comprising the nucleotide sequence of SEQ ID NO: 33 and a methylation primer comprising the nucleotide sequence of SEQ ID NO: 35;
3) a methylation primer comprising the nucleotide sequence of SEQ ID NO: 37 and a methylation primer comprising the nucleotide sequence of SEQ ID NO: 39;
4) a methylation primer comprising the nucleotide sequence of SEQ ID NO: 41 and a methylation primer comprising the nucleotide sequence of SEQ ID NO: 43; and
5) a methylation primer comprising the nucleotide sequence of SEQ ID NO: 45 and a methylation primer comprising the nucleotide sequence of SEQ ID NO: 47, and
at least one unmethylation primer pair selected from the group consisting of:
1) an unmethylation primer comprising the nucleotide sequence of SEQ ID NO: 30 and an unmethylation primer comprising the nucleotide sequence of SEQ ID NO: 32;
2) an unmethylation primer comprising the nucleotide sequence of SEQ ID NO: 34 and an unmethylation primer comprising the nucleotide sequence of SEQ ID NO: 36;
3) an unmethylation primer comprising the nucleotide sequence of SEQ ID NO: 38 and an unmethylation primer comprising the nucleotide sequence of SEQ ID NO: 40;
4) an unmethylation primer comprising the nucleotide sequence of SEQ ID NO: 42 and an unmethylation primer comprising the nucleotide sequence of SEQ ID NO: 44; and
5) an unmethylation primer comprising the nucleotide sequence of SEQ ID NO: 46 and an unmethylation primer comprising the nucleotide sequence of SEQ ID NO: 48.

2. A kit for assessing colorectal cancer in a subject comprising:
methylation specific primers for at least two biomarkers selected from: PROM1, SARP1 and MSF1,
wherein the methylation specific primers for PROM1 comprise:
a) at least one methylation primer pair selected from the group consisting of:
1) a methylation primer comprising the nucleotide sequence of SEQ ID NO: 1 and a methylation primer comprising the nucleotide sequence of SEQ ID NO: 3;

2) a methylation primer comprising the nucleotide sequence of SEQ ID NO: 5 and a methylation primer comprising the nucleotide sequence of SEQ ID NO: 7; and 3) a methylation primer comprising the nucleotide sequence of SEQ ID NO: 9 and a methylation primer comprising the nucleotide sequence of SEQ ID NO: 11, and b) at least one unmethylation primer pair selected from the group consisting of:

1) an unmethylation primer comprising the nucleotide sequence of SEQ ID NO: 2 and an unmethylation primer comprising the nucleotide sequence of SEQ ID NO: 4;

2) an unmethylation primer comprising the nucleotide sequence of SEQ ID NO: 6 and an unmethylation primer comprising the nucleotide sequence of SEQ ID NO: 8; and 3) an unmethylation primer comprising the nucleotide sequence of SEQ ID NO: 10 and an unmethylation primer comprising the nucleotide sequence of SEQ ID NO: 12, wherein the methylation specific primers for SARP1 comprise:

a) at least one methylation primer pair selected from the group consisting of:

1) a methylation primer comprising the nucleotide sequence of SEQ ID NO: 13 and a methylation primer comprising the nucleotide sequence of SEQ ID NO: 15;

2) a methylation primer comprising the nucleotide sequence of SEQ ID NO: 17 and a methylation primer comprising the nucleotide sequence of SEQ ID NO: 19;

3) a methylation primer comprising the nucleotide sequence of SEQ ID NO: 21 and a methylation primer comprising the nucleotide sequence of SEQ ID NO: 23; and 4) a methylation primer comprising the nucleotide sequence of SEQ ID NO: 25 and a methylation primer comprising the nucleotide sequence of SEQ ID NO: 27, and b) at least one unmethylation primer pair selected from the group consisting of:

1) an unmethylation primer comprising the nucleotide sequence of SEQ ID NO: 14 and an unmethylation primer comprising the nucleotide sequence of SEQ ID NO: 16;

2) an unmethylation primer comprising the nucleotide sequence of SEQ ID NO: 18 and an unmethylation primer comprising the nucleotide sequence of SEQ ID NO: 20;

3) an unmethylation primer comprising the nucleotide sequence of SEQ ID NO: 22 and an unmethylation primer comprising the nucleotide sequence of SEQ ID NO: 24; and 4) an unmethylation primer comprising the nucleotide sequence of SEQ ID NO: 26 and an unmethylation primer comprising the nucleotide sequence of SEQ ID NO: 28, wherein methylation specific primers for MSF1 comprise:

a) at least one methylation primer pair selected from the group consisting of:

1) a methylation primer comprising the nucleotide sequence of SEQ ID NO: 29 and a methylation primer comprising the nucleotide sequence of SEQ ID NO: 31;

2) a methylation primer comprising the nucleotide sequence of SEQ ID NO: 33 and a methylation primer comprising the nucleotide sequence of SEQ ID NO: 35;

3) a methylation primer comprising the nucleotide sequence of SEQ ID NO: 37 and a methylation primer comprising the nucleotide sequence of SEQ ID NO: 39;

4) a methylation primer comprising the nucleotide sequence of SEQ ID NO: 41 and a methylation primer comprising the nucleotide sequence of SEQ ID NO: 43; and 5) a methylation primer comprising the nucleotide sequence of SEQ ID NO: 45 and a methylation primer comprising the nucleotide sequence of SEQ ID NO: 47, and b) at least one unmethylation primer pair selected from the group consisting of:

1) an unmethylation primer comprising the nucleotide sequence of SEQ ID NO: 30 and an unmethylation primer comprising the nucleotide sequence of SEQ ID NO: 32;

2) an unmethylation primer comprising the nucleotide sequence of SEQ ID NO: 34 and an unmethylation primer comprising the nucleotide sequence of SEQ ID NO: 36;

3) an unmethylation primer comprising the nucleotide sequence of SEQ ID NO: 38 and an unmethylation primer comprising the nucleotide sequence of SEQ ID NO: 40;

4) an unmethylation primer comprising the nucleotide sequence of SEQ ID NO: 42 and an unmethylation primer comprising the nucleotide sequence of SEQ ID NO: 44; and 5) an unmethylation primer comprising the nucleotide sequence of SEQ ID NO: 46 and an unmethylation primer comprising the nucleotide sequence of SEQ ID NO: 48.

* * * * *